US006264948B1

(12) United States Patent
Wong et al.

(10) Patent No.: US 6,264,948 B1
(45) Date of Patent: Jul. 24, 2001

(54) METHODS AND COMPOSITIONS FOR INHIBITING TUMOR CELL GROWTH

(75) Inventors: David T. W. Wong, Newton; Peter F. Weller, Wellesley, both of MA (US)

(73) Assignee: Beth Israel Deaconess Hospital, Inc., Boston, MA (US)

( * ) Notice: Subject to any disclaimer, the term of this patent is extended or adjusted under 35 U.S.C. 154(b) by 0 days.

(21) Appl. No.: 09/207,445

(22) Filed: Dec. 8, 1998

Related U.S. Application Data

(60) Provisional application No. 60/068,267, filed on Dec. 19, 1997.

(51) Int. Cl.[7] ........................ A61K 39/395; A61K 35/14; C07K 1/00; C07K 14/00; C07K 17/00

(52) U.S. Cl. .................................... 424/130.1; 424/145.1; 424/152.1; 424/153.1; 424/155.1; 530/350; 530/351; 530/380; 530/386; 530/387.1

(58) Field of Search ............................. 424/130.1, 145.1, 424/152.1, 153.1, 155.1; 530/350, 351, 380, 386, 387.1

(56) References Cited

U.S. PATENT DOCUMENTS 5,837,713 11/1998 Gleich .
5,849,719 12/1998 Carson et al. .

FOREIGN PATENT DOCUMENTS 2019408 10/1979 (GB) .

OTHER PUBLICATIONS

Johnson, Randall K. and Goldin, Abraham. The clinical impact of screening and other eperimental tumor studies. Cancer Treatment Reviews 2:1–31, 1975.*

Wong, et al. Eosinophil ablation and tumor development. Oral Oncology 35:496–501, 1975.*

Ashman et al. (1990) Leukemia Research, vol. 14, No. 7, pp. 637–644, especially pp. 637 (abstract) and table 1.

Dibbert et al (1998) Blood.Aug. 1, vol. 92, No. 3, pp. 778–783, epecially pp. 778 and 782.

Erger et al (1998) International Archives of Allergy and Immunology. vol. 115, pp. 24–32.

Resnick et al (1995) Feb., Gastroenterology. vol. 108, No. 12, pp. 409–416, especially pp. 408 (abstract), 413, 415 and figure 6.

Satoh, et al (1994) Immunology. vol. 83, pp. 308–312, especially pp. 308 and 311.

Stefanini et al (1991) Cancer. Aug. 1, vol. 68, No. 3, pp. 543–548, especially figure 2.

Arnheiter et al., *Nature*, 294, 278–280 (1981).

Butler, 1982, *Methods Enzymol.*, 73: 482–523.

Darwiche et al., 1993, *Cancer Res.*, 53: 2287–2299.

Devos et al., 1995, *J. Leuk. Biol.*, 57: 813–819.

Dymecki et al., 1992, *J. Biol. Chem.*, 267: 4815–4823.

Guide for the Care and Use of Laboratory Animals, *DHHS Publication No. (NIH) 85–23*, Revised 1985.

Ghiabi et al., 1992, *Cancer Res.*, 52: 389–393.

Goldsmith et al., 1987, *Otolaryngology—Head and Nech Surgery*, 96: 319–324.

Greenberg et al., 1995, *Proc. natl. Acad. Sci. U.S.A.*, 92: 3439–3443.

Horiuchi et al, 1993, *J. Surg. Oncol.*, 53: 92–96.

Hubbard et al., 1989, *J. Clin. Invest.*, 84: 1349–1354.

Humason, 1979, *Animal Tissue Techniques, 4th Edition.*, W.H. Freeman and Company, San Francisco.

Iwasaki et al., 1986 *Cancer*, 58: 1321–1327.

Kapp and Livolsi, 1983, *Gynecologic Oncology*, 16: 19–30.

Kolb and Muller, 1979, *Br. J. Cancer*, 40: 410–416.

Kuger–Krassagakes et al., 1993, *Eur. J. Immunol.*, 23: 992–995.

Lowe and Fletcher, 1984, *Histopathology*, 8: 627–632.

Lowe et al., 1984, *Histopathology*, 8: 627–632.

Lowe and Fletcher, 1984, *J. Clin. Pathol.*, 37: 500–502.

Maggio, E. (ed.), 1980, Enzyme Immunoassay, CRC press, Boca Raton, FL) or radioimmunoassays (RIA).

Major, et al., 1996, *Gynocol. Oncol.*, 66: 122–132.

McClellan et al., 1986, in: Life–span Radiation Effects Studies in Animals: What Can They Tell Us?, eds. Thompson and Mahaffey CONF–830951, pp. 74–96, Office of Scientific and Technical Information, D.o.E., Richland, WA.

McGinnis et al., 1989, *Cancer Res.*, 49: 5989–5993.

Pretlow et al., 1983 *Cancer Res.*, 43: 2997–3000.

Rollins and Sunday, 1991, *Mol. Cell. Biol.*, 11: 3125–3131.

Tepper et al., 1989, *Cell*, 57: 503–512.

Tepper et al., 1992, *Science*, 257: 548–551.

Voller et al., 1978, *J. Clin. Pathol.*, 31: 507–520.

Weller, 1991, *New England J. Med*, 324: 1110–1118.

Wong et al., 1990, *J. Exp. Med.*, 172: 673–681.

Yamaguchi et al., 1988, *J. Exp. Med.*, 167: 43–56.

Yang et al., 1997, *Am. J. Pathol.*, 151: 813–819.

* cited by examiner

*Primary Examiner*—Sheela Huff
*Assistant Examiner*—Alana M. Harris
(74) *Attorney, Agent, or Firm*—Palmer & Dodge, LLP; Kathleen M. Williams

(57) ABSTRACT

A method of suppressing tumor cell growth, comprising administering to a mammal in need thereof an amount of an inhibitor of eosinophilia sufficient to result in suppression of tumor cell growth is disclosed.

12 Claims, No Drawings

METHODS AND COMPOSITIONS FOR INHIBITING TUMOR CELL GROWTH

This application claims the benefit under 35 U.S.C. 119(e) of provision Application No. 60/068,267, filed Dec. 19, 1997.

This invention was supported by NIH Grant Nos. DE 08680 and DE 00323 and the government has certain rights to the invention.

FIELD OF THE INVENTION

The invention relates in general to the field of cancer prevention and treatment.

BACKGROUND OF THE INVENTION

The inhibition of malignant cell induction and proliferation is the primary goal of cancer prevention and treatment. Physiological changes that are coincident with the occurrence of cancer may indicate phenomena that are either causative or protective with regard to the development and progression of the disease and are, therefore, of significant interest to clinical researchers.

Eosinophils are granulocytic leukocytes with bi-lobed nuclei, named for their property of staining red in eosin dye. Their production from bone marrow stem cells, maturation and activation occur specifically in response to signals mediated by interleukin-5 (Weller, 1991, *New England J. Med,* 324: 1110–1118). These cells reside largely in epithelium-lined tissues that are in contact with the environment, such as the gastrointestinal- and lower genitourinary tracts, as well as the respiratory epithelium (Devos et al., 1995, *J. Leuk. Biol.,* 57: 813–819; Weller, 1991, supra; Wong et al., 1990, *J. Exp. Med.,* 172: 673–681).

Tissue eosinophilia in malignancies of epithelial origin has been reported since 1893 (Reinback, 1893, *Arch. Klin. Chir.,* 46: 486–562); however, the role of the eosinophil in the cancer etiology remains unclear. Eosinophil influx has been shown to be associated with a number of human tumors, primarily carcinomas (Goldsmith et al., 1987, *Otolaryngology-Head and Neck Surgery,* 96: 319–[−3]24; Iwasaki et al., 1986, *Cancer,* 58: 1321–1327; Kolb and Muller, 1979, *Br. J. Cancer,* 40: 410–416; Lowe and Fletcher, 1984, *Histopathology,* 8: 627–632; Loew et al., 1984, *Histopathology,* 8: 619–625; McGinnis et al., 1989, *Cancer Res.,* 49: 5989–5993; Pretlow et al., 1983, *Cancer Res.,* 43: 2997–3000).

While eosinophils have been found not to suppress growth in interleukin-5 transfected tumor cells (Kuger-Krasagakes et al., 1993, *Eur. J. Immunol.,* 23: 992–995), suppression of tumor development has been demonstrated in cells transfected with genes encoding either IL-4 (Tepper et al., 1989, *Cell,* 57: 503–512) or monocyte chemoattractant MCP-1/JE (Rollins and Sunday, 1991, *Mol. Cell. Biol.,* 11: 3125–3131) through a host-reactive inflammatory response that consists of significant tissue eosinophilia. Using antibodies that specifically block the accumulation of granulocytes at the site of inflammation, it further has been demonstrated that eosinophils are directly involved in the observed IL-4-mediated tumor cytotoxicity (Tepper et al., 1992, *Science,* 257: 548–551).

Published clinical evidence supports both host-protective and tumor-inducing roles for eosinophils in cancer, thereby providing little or no therapeutic guidance. Stromal eosinophilia has been suggested as a favorable prognostic indicator in cases of human neoplasms, including head and neck cancers (Goldsmith et al., 1987, supra), which supports the hypothesis of a "protective" role of eosinophils in cancer. Increased survival and decreased metastasis correlate positively with the level of tumor associated tissue eosinophilia (TATE) in patients suffering colonic carcinoma (Pretlow et al., 1983, supra) and tumors of the uterine cervix (Kapp and Livolsi, 1983, *Gynecologic Oncology,* 16: 19–30). Heavy eosinophilic infiltration has been suggested as indicating an unfavorable prognosis in well-differentiated squamous cell carcinomas of the oral cavity (Horiuchi et al., 1993, *J. Surg. Oncol.,* 53: 92–96); however, this finding is contradicted by reports that massive tissue eosinophilia is associated with a favorable prognosis in cases of squamous cell carcinoma of the oral cavity, external genitalia, and anus (Lowe and Fletcher, 1984, *Histopathology,* 8: 627–632) as well as tumors of the bladder (Lowe and Fletcher, 1984, *J. Clin. Pathol.,* 37: 500–502). It has also been reported that interleukin-4 transfected tumor cells lose their ability to form tumors if eosinophils are present (Tepper et al., 1989, *Cell,* 57: 503–512).

There is a need in the art for improved methods for the prevention and treatment of cancer.

SUMMARY OF THE INVENTION

The invention provides a method of suppressing tumor cell growth, comprising administration to a mammal in need thereof of an amount of an inhibitor of eosinophilia sufficient to result in a delay in the onset- or reduction in the rate of tumor cell growth.

As used herein, the term "suppressing" refers to reducing the frequency of tumor formation in individuals who are at risk of developing tumors. A 2- to 10-fold reduction in the percentage of at-risk individuals at who form tumors after treatment with an inhibitor of eosinophilia, relative to the percentage of at-risk individuals who form tumors when left untreated, is required for treatment to be considered effective according to the invention. Preferably, the reduction is in the range of 20- to 100-fold, or even to 200- to 1,000-fold. The term "suppressing" additionally refers to increasing the length of time required for tumor cells to arise after exposure to a tumorigenic substance (or, in the case of subjects with a genetic propensity to develop tumors, birth), reducing the rate of cell division in an existing tumor or causing regression (shrinkage in cell number) of an existing tumor. A prolongation of the onset of tumor cell growth that is indicative of effective treatment according to the invention is at least 4-fold, preferably from 5- to 10-fold, and even from 20- to 100-fold the average length of time until the first tumor cells are observed in control individuals in whom eosinophilia has not been blocked. In order to be judged effective, an inhibitor of eosiniophilia must mediate a reduction in the rate of cell division in an existing tumor of at least 2- to 10-fold, preferably 20- to 100-fold and even up to 200- to 1000-fold. A regression of at least 50% of tumor burden in treated individuals relative to untreated controls is indicative of effective treatment according to the invention; preferably, such a loss of tumor cell mass is up to 75% or even 100% of the total present.

A "tumor cell" is any cell that has undergone one or more rounds of cell division that take place outside the course of the growth of an organism to maturity, normal biological function (e.g. the production of hematopoietic cells or gametes from stem cells) or wound healing, characterized by a loss of contact inhibition or substrate dependence or changes in morphology and/or protein production.

As used herein, "malignant" refers to cancerous cell growth.

In contrast, "normal tissue" is defined as being one or more cells that are not tumor cells and/or that do not possess a malignant phenotype (that is, that do not display cancerous cell growth), as defined above.

As used herein to describe tumor cells, the term "growth" is defined as including induction (determination that a normal cell will become a tumor cell), transformation (differentiation of a normal cell to a tumor cell, whether or not such transformation is oncogenic) and proliferation.

As used herein, the term "mammal" refers to any member of the Class Mammalia, including a human.

Preferably, the mammal is a human.

As used herein, the term "inhibitor" is defined as any substance which blocks or reverses the influx of eosinophils into tumor tissue or an adjacent site, whether directly or by inhibiting a signalling pathway that results in such infiltration. Such blocking or reversal may occur at the level of synthesis of a substance that promotes the maturation or migration of eosinophils. Alternatively, it may be the native activity of such a substance which is blocked or reversed, either directly, or by inhibition of downstream target molecules, e.g. in a signalling cascade or biosynthetic pathway. An inhibitor may exert an opposing function (for example, activation of a receptor that is opposed by the substance being inhibited, or of a receptor that regulates a signalling cascade that results in an opposing function to that controlled by a receptor activated by the substance). An inhibitor may modify the substance that promotes eosinophil infiltration, for example by altering its state of phosphorylation or glycosylation or by cleaving the substance. An inhibitor, such as an antibody, may bind to the substance and either sterically hinder an active site or change the conformation of the substance; it may also, in the case in which the substance acts in dimerized or multimerized form, be an inactive monomer which binds the substance and ties it up in a non-functional unit, which may either remain in place or be degraded by cellular mechanisms.

Preferably, the inhibitor inhibits a cytokine that influences the maturation of eosinophils, wherein inhibition of the cytokine results in inhibition of eosinophil influx into tumor tissue or an adjacent site; more preferably, this inhibitor inhibits a Colony Stimulating Factor (CSF); most preferably, this inhibitor inhibits IL-5.

As used here, the term "maturation" refers to the process by which hematopoietic stem cells become eosinophils.

It is preferred that the inhibitor of IL-5 is an anti-IL-5 antibody.

Preferably the tumor comprises cells that are malignant.

Further features and advantages of the invention will become more fully apparent in the following description of the embodiments and drawings thereof, and from the claims.

DESCRIPTION OF THE INVENTION

The invention is based on the recognition that inhibition of eosinophil influx into tissue that has been exposed to an amount of a carcinogen sufficient to cause tumor cell growth results in the suppression of such growth, in terms of delaying the onset of tumorigenesis, the number of tumors formed and the total mass of such tissue. Animal models are described herein for the suppression of tumor cell development and proliferation via inhibition of eosinophil infiltration into a site at which such growth has been induced.

It has been shown that eosinophils progressively infiltrate into sites of chemically- induced oral cancer development in a hamster model (Ghiabi et al., 1992, *Cancer Res.,* 52: 389–393).

Inhibitors Useful According to the Invention

Suppression of tumor cell growth according to the methods of the invention, e.g. by blocking eosinophilia in a tissue in which there is the expectation that such growth will occur, due to either known genetic propensity toward- or documented prior occurrence of it or due to exposure of that tissue to a mutagen, can be brought about by intervention at either of two levels.

The invention provides a means by which to counteract inhibition of the development of the broad group of cells categorized as leukocytes, of which eosinophils represent one member. Their development from various hematopoietic stem cells is mediated by the Colony Stimulating Factor (CSF) family of proteins. Administration of a CSF inhibitor is believed to be effective in blocking leukocyte development and function; the subset of leukocyte cell types affected is determined by the identity of the CSF molecule inhibited. Suitable direct inhibitors include CSF analogues (which would compete with a given CSF for binding to sites on receptors or other molecules), antisense RNA, CSF mRNA-specific ribozymes and antibodies directed at CSF proteins. By similar methods, CSF ftunction can be inhibited indirectly, i.e. by blocking the synthesis or activities of downstream target molecules, such as signalling molecules or growth factors, that participate in the leukocyte induction pathway.

One CSF, interleukin-5 (IL-5), positively regulates the pathway that results in maturation, terminal differentiation and release of eosinophils (Yamaguchi et al., 1988, *J. Exp. Med.,* 167: 43–56; Yamaguchi et al., 1988, *J. Exp. Med.,* 167: 1737–1742); therefore, inhibition of the production or function of this molecule by any of the above methods may be performed according to the methods of the invention in order to negate the impact of eosinophil infiltration on tumor cell growth. Monoclonal antibodies directed against human IL-5 are known in the art as TRFK-5 (Schering-Plough Research Institute) and MAB205 (R & D Systems, Minneapolis, Minn.). Both are murine monoclonal antibodies directed against human IL-5. TRFK-5 is heterospecifically reactive; in other words, although the antibody was raised against a human protein, it recognizes IL-5 homologues in other species as well. Its use to inhibit eosinophilia in an animal model of the suppression of tumor cell growth is exemplified below in Example 1. Anti-IL-5 antibodies may be produced according to methods well known in the art (see below). Purified, recombinant human IL-5 protein against which to raise antibodies is commercially available; for example, human IL-5 can be obtained from R & D Systems, Minneapolis, Minn. (Cat. No. 205-IL).

Generation of Antibodies

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

Preparation of Antibodies

1. Polyclonal Antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.,* 267: 4815–4823). The serum is titered against protein antigen by ELISA or alternatively by dot or spot blotting (Boersma and Van Leeuwen, 1994, *J. Neurosci. Methods,* 51: 317). At the same time, the antiserum may be used in tissue sections. The serum is shown to react strongly with the appropriate peptides by ELISA, for example, following the procedures of Green et al., 1982, *Cell,* 28: 477–487.

2. Monoclonal Antibodies.

Techniques for preparing monoclonal antibodies are well known, and monoclonal antibodies may be prepared using any candidate antigen whose level is to be measured at a site of potential tumor cell growth or in tissue surrounding tumor cells, such as a Colony Stimulating Factor (e.g. IL-5) or other cytokine, preferably bound to a carrier, as described by Amheiter et al., *Nature,* 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" a protein.

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons,* 2:1–7, Microbiological Associates Quarterly Publication, Walkersville, Md.; Voller et al., 1978, *J. Clin, Pathol.,* 31: 507–520; U.S. Reissue Pat. No. 31,006; UK Patent 2,019,408; Butler, 1981, *Methods Enzymol.,* 73: 482–523; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence of a protein that is to be acted against by a candidate inhibitor of tumor cell growth according to the present invention, immunohistochemistry techniques are preferably used. It will be apparent to one skilled in the art that the antibody molecule will have to labeled to facilitate easy detection of a target protein. Techniques for labeling antibody molecules are well known to those skilled in the art (see Harlour and Lane, 1989, *Antibodies*, Cold Spring Harbor Laboratory, pp. 1–726).

Alternatively, other techniques can be used to detect the target proteins, including chromatographic methods such as SDS PAGE, isoelectric focusing, Western blotting, HPLC and capillary electrophoresis.

Monoclonal antibody-producing hybridomas (or polyclonal sera) can be screened for antibody binding to the target protein. By antibodies, we include constructions using the binding (variable) region of such antibodies, and other antibody modifications. Thus, an antibody useful in the invention may comprise whole antibodies, antibody fragments, polyfunctional antibody aggregates, or in general any substance comprising one or more specific binding sites from an antibody. The antibody fragments may be fragments such as Fv, Fab and $F(ab')_2$ fragments or any derivatives thereof, such as a single chain Fv fragments. The antibodies or antibody fragments may be non-recombinant, recombinant or humanized. The antibody may be of any immunoglobulin isotype, e.g., IgG, IgM, and so forth. In addition, aggregates, polymers, derivatives and conjugates of immunoglobulins or their fragments can be used where appropriate.

Methods for Testing Inhibition of Eosinophilia

In order to test the efficacy of inhibitors of eosinophil influx into a site of potential tumor cell growth or into the tissue surrounding tumor cells, the candidate inhibitor is tested in an animal model of tumor cell growth. Several animal models useful according to the invention are known in the art. A first requirement of such a model is demonstrated proof that eosinophils do, indeed, infiltrate tumor tissue or a site adjacent to it in that organism. Given that such observations also have been made in humans (see above), the results of inhibitor testing performed in any of these several systems will be applicable to the clinical treatment of human tumor cell growth. If uncertainty exists as to whether tumor cell induction and proliferation at a given anatomical site is accompanied by eosinophil influx, this can be determined by the methods described in the art below.

Having first selected the experimental organism and site at which the animal will be exposed to a tumor-promoting mutagen, the surface area to which the substance is to be applied is determined, as is dosage and a method of administration. After establishing the parameters for tumor induction in an otherwise untreated subject, a typical experiment comprises test and control groups of animals that are comparably dosed with the mutagen on the same day. By "comparably", it is meant that a region of the same shape and surface area is dosed with the same amount and concentration of the mutagen at the same anatomical location. One group receives an appropriate dosage of the candidate inhibitor of eosinophilia in a compatible carrier, while the other is dosed only with the carrier, and tumor cell growth, as defined below in Example 1, is monitored over the course of many days.

At a point following the initial treatment with the mutagen, a subset of animals in either of the two groups is sacrificed. The test sites are harvested, sectioned and subjected to histological examination to measure the density of eosinophils that have infiltrated the tissue. The number of tumors and total tumor load (see below) are determined, as is the approximate time of tumorigenesis. Results within each group are collated, and then compared to those derived from the other group. A positive result, i.e. one in which eosinophils are seen to be reduced in the mutagenized area of test subjects relative to controls, indicates that the candidate compound is therapeutically useful according to the invention. A reduction in the density of eosinophils infiltrating the test site of at least twofold is indicative of tumor suppression according to the invention. A range of about 2-fold to about 2000-fold (or even up to 10,000-fold) is indicative of tumor suppression, for example, in the range of about 100- to 200-fold.

Administration, Dosage and Pharmacological Formulation of an Inhibitor a. Administration Depending upon the intended target of the inhibitor of eosinophilia, different routes of administration may be used. One may attempt inhibition at one of two critical steps: (a) the development and/or release of mature eosinophils, which requires that the inhibitor be directed at hematopoietic stem cells via systemic administration of the drug, or (b) recruitment of eosinophils to the site of actual or anticipated tumor cell growth. While the recruitment process is not yet understood, it is anticipated that when the underlying mechanism is elucidated, inhibitory compounds should be directed to the site to be treated, which can be accomplished by systemic or topical administration of the candidate compound.

1. Systemic Administration of an Inhibitor Compound.

In cases in which activity of the inhibitor is required at a site that is remote relative to the that of tumor cell induction or growth, systemic administration of a drug is generally appropriate. Methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced inhibitor or may, instead, comprise cells that produce and secrete the inhibitory substance.

Alternatively, systemic administration is advantageous when inhibitor must be delivered to a target site that is accessible to topical application, but in which environment (such as the digestive tract) the native activity of the inhibitor might be compromised, e.g. by digestive enzymes or extremes of pH.

2. Topical Application of Inhibitor

It is contemplated that global administration of the inhibitor to an animal is not needed in order to achieve a highly localized effect. Given that an epithelial tumor is, by definition, on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Topical compositions comprising an inhibitor can take any of several physical forms, as summarized below:

(i) A liquid, such as a tincture or lotion, which may be applied by pouring, dropping or "painting" (i. e. spreading manually or with a brush or other applicator such as a spatula).

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the site of potential or actual tumor cell growth or, alternatively, applied as a nebulized spray.

(iv) An liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of an inhibitor.

In a specialized instance, the internal surface is that of the lung. Epithelial tumors in the lung often result from long-term exposure to tobacco smoke or other chemical irritants. In such a case the most expedient route of administration for inhibitor is via inhalation, either of a liquid aerosol of (d) or of a nebulized powder of (c). Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.,* 84: 1349–1354).

Note that in some cases, the internal surface in question may, for example, be found along the gastrointestinal tract lining; in such a case, topical application would comprise taking the drug via an oral route, whether in liquid, gel or solid form.

b. Dosage

Dosage is calculated based upon the systemic dose demonstrated to be effective. For example, the test hamsters of Example 1, below, received 5 mg doses of inhibitor intraperitoneally every second week over a 14-week period; each dose was, therefore, approximately 58.8 mg/kg of total body weight at the time of administration, based upon a body weight of 85 g. Taking into account the half-life of the native activity of a given inhibitor in blood serum, the mean circulating dosage throughout the week is estimated in mg/kg of total body weight. Such a dosage may range from 10 $\mu$g to 100 mg; preferably, it is from 100 $\mu$g to 10 mg. The volume of cells to be treated is then calculated. If administration is to be topical, then V=target site surface area×depth of affected cell layers; otherwise, the whole-body volume of the individual to be treated is estimated. This figure is converted to kg, assuming a density of approximately equal to 1, and the whole body dosage is divided by that number. The concentration of inhibitor in the chosen carrier composition is then adjusted such that the required dosage is delivered in a convenient volume.

c. Pharmacological Formulation

In the case of liquids, ointments and liquid-based aerosols, the preferred solvent is an aqueous medium with an ionic balance that mimics physiological salt levels in order to preserve activity of the inhibitor and to avoid changes in osmotic pressure for the cells to be contacted with the composition. An example of such medium is a low-ionic-strength saline solution.

Lipid-, other hydrocarbon-, fluorocarbon- or halogen-based media also should be formulated such that they maintain a physiological salt balance.

Dry powders comprising a protein or carbohydrate may be produced via air-drying of a precipitate or by lyophilization; in some instances, an inhibitor may be an organic or inorganic salt, commercially known and available as a dry powder or as crystals. In either case, it is desirable to compound the inhibitor with a bulking agent, such as are commonly known in the art, for ease of handling.

An inhibitor of eosinophil influx into a site of tumor cell growth may comprise a protein, carbohydrate or other biodegradable substance; therefore, depending upon the route of administration, it may be necessary to encapsulate or buffer it in such a way as to protect it from degradation (for example, by digestive enzymes, acid and base), at least until it reaches its target, by such methods as are well known in the pharmacological art.

The invention is illustrated by the following nonlimiting examples wherein the following materials and methods are employed. The entire disclosure of each of the literature references cited hereinafter are incorporated by reference herein.

Example 1 describes the use of an anti-IL-5 monoclonal antibody (TRFK-5) preparation to neutralize IL-5 activities in vivo and demonstrates its inhibitory effect on oral epithelial tumor cell induction and growth in the hamster cheek pouch model; however, epithelial tumors may arise in cutaneous (external), gastric, esophageal, intestinal, nasal, sinus, tracheobronchial, pulmonary, vaginal, anal or other epithelial tissues. Each of Examples 2 through 6 presents a model in which a candidate inhibitor is administered via any of the several systemic or topical routes detailed above and assessed for efficacy at inhibiting tumor cell growth which has been induced by any of a variety of methods in a different epithelial tissue, including those of the ovary, lung, prostate, urinary bladder and uterine cervix, respectively. As discussed above, vidence exists that in certain of these tissues, eosinophilia is a favorable prognostic indicator. The examples provide models in which such assumptions, where present, may be supported or weakened as inhibitors of eosinophilia are tested for their ability to suppress tumor cell growth according to the invention in these several tissues.

EXAMPLE 1

In order to examine the role of an inhibitor of eosinophilia on epithelial tumor cell growth, the well-established carcinogen-induced Syrian hamster cheek pouch model was used. 19 male Syrian golden hamsters, 60–90 days old, 81–90 grams, were purchased from Charles River Laboratory (Wilmington, Mass.). All animals were treated according to the “Guide for the Care and Use of Laboratory Animals” (DHHS Publication No. (NIH) 85-23, Revised 1985). Animals were maintained in separate cages (1 animal per cage) in an air-conditioned (24° C.) animal room on a 12-hour light, 12-hour dark cycle, and fed with a commercial stock diet (Purina Formula Chow) and tap water ad libitum (protocol 48-R95), over a fourteen week period in the animal care facilities at the Harvard School of Public Health.

Hamsters were divided into 4 groups. Group I consisted of 5 hamsters which were treated every other day (three timesper week) with a 0.5% solution of 7,12 dimethylbenz (a)anthracene (DMBA, D-3254; Sigma Chemical Co., St. Louis, Mo.) dissolved in mineral oil (U.S.P.), painted in the left cheek pouch with a No. 4 soft sable brush. Group II consisted of 4 hamsters which were treated with mineral oil only, in the same manner. Group III had 5 hamsters which received the 0.5%DMBA in mineral oil in the same manner. Additionally, 5 mg of anti-IL-5 mono-specific antibodies (TRFK-5, 6.46 mg/ml, lot #4TRFK-4; supplied by the Schering Plough Research Institute) were administered every second week via intraperitoneal injection. Group IV, with 5 hamsters, received the 0.5% DMBA in mineral oil in the same manner, in addition to 5 mg of control antibodies to bacterial β-galactosidase (GL-1 13 Control Ab, 6.0 mg/ml. lot #V271939-003) via intraperitoneal injection, every second week.

Weekly observations included gross examination of the cheek pouches, made easy with a nasal speculum, and recording findings of leukoplakia, erythroplakia, erythema, hyperkeratosis, tumor size, number, and morphology, and animal body weight.

After the fourteenth week, animals were sacrificed by $CO_2$ asphyxiation and their left cheek pouches harvested. Cheek pouches were photographed, and diagrammed to record final clinical findings. Dimensions of individual tumors were also measured and recorded. Tumors were then excised and fixed in 10% formalin, processed and embedded in paraffin, sectioned, mounted on slides and stained for microscopy, all by standard histological procedures (see Humason, 1979, *Animal Tissue Techniques, 4th Edition*, W.H. Freeman and Company, San Francisco). The femurs of representative animals from each of the four groups were also harvested.

To facilitate the identification of eosinophils in examined sections, all slides were stained with Fisher Giemsa (SG-28). Eosinophils stained in this manner exhibit bright orange fluorescence when viewed with a rhodamine filter at 552 nm. Eosinophils were then quantified, and the extent of tumor invasiveness and differentiation was assessed. Tumor burden was calculated by using spherical volume, $0.75\pi r^3$, as most tumors were papulomatous and spherical.

Those that were more plaque-like and elliptical required the calculation $LW^2(0.52)$, where L=length and W=width. Total volume was then divided by the number of tumors to obtain mean tumor burden.

The Effect of anti-IL-5 Antibody on Tissue Eosinophilia

The ability of anti-IL-5 antibody (TRFK-5) to block eosinophil infiltration into the stromal tissue surrounding chemically induced squamous cell carcinomas in the hamster cheek pouch was assayed. Eosinophil quantification, in Giemsa-stained tumor specimens under a rhodamine filter, was performed. The average number of eosinophils in tumor sections from each group are shown in Table 1.

TABLE 1

| Group | # of Eosinophils |
|---|---|
| I | 157 |
| II | 0 |
| III | 1.7 |
| IV | 128 |

Statistical analysis by Pearson's $Chi^2$and Fisher's exact test revealed that there is a relationship between the number of eosinophils observed, and whether the animal received TRFK-5, with p=0.001 and R (correlation coefficient)=−0.5480. Thus animals receiving TRFK-5 had significantly fewer eosinophils than those who did not.

Tumor Burden in Hamsters Treated with anti-IL-5 Antibodies

The possible relationship between TATE and tumor burden was examined. The results are shown in Table 2.

TABLE 2

| Group | Tumor Burden ($cm^3$) |
|---|---|
| I | 0.123 |
| II | 0 |
| III | 0.027 |
| IV | 0.463 |

Group I had a 4.6 fold greater tumor burden, at 0.123 $cm^3$, than Group III, 0.027 $cm^3$, which had received TRFK-5. Interestingly, the greatest tumor burden was witnessed in Group IV, which at 0.0463 $cm^3$ was 3.8-fold greater than that found in Group I, which received DMBA only. It should be noted that comparing Group III and IV, the difference in tumor burden is 17.1-fold.

Regression analysis revealed that the number of eosinophils had no relation to average tumor volume in each animal, β=0.00002 (CI −0.0004–0.0009). Neither was there a relationship between the number of eosinophils and the total tumor volume in each animal β=0.0013 (CI −0.0018–0.0044).

Timing of Tumor Development in Hamsters Treated With TRFK-5

The formation and growth kinetics of tumors in animals treated with anti-IL-5 antibodies were quantified. Visible tumor development was delayed in animals receiving TRFK-5 as compared to groups I and IV. The numbers of animals that are seen to have developed tumors over time are shown in Table 3.

TABLE 3

| Group | week 6 | week 7 | week 8 | week 9 | week 12 |
|---|---|---|---|---|---|
| I | 0 | 3 | 3 | 4 | 5 |
| II | 0 | 0 | 0 | 0 | 0 |

TABLE 3-continued

| Group | week 6 | week 7 | week 8 | week 9 | week 12 |
|---|---|---|---|---|---|
| III | 0 | 0 | 1 | 1 | 3 |
| IV | 1 | 3 | 3 | 4 | 5 |

Group III animals did not develop tumors until week 8, while group I and IV animals began developing tumors in weeks 6 and 7 respectively. By week 9, 80% of animals in groups I and IV had developed tumors as opposed to only 20% in group III. 60% of group III animals had developed tumors by week 12. At this time all the animals in groups I and IV were affected.

These results demonstrate that when eosinophilia of the stromal tissues adjacent to chemically-induced squamous cell carcinomas in the hamster cheek pouch is successfully blocked, tumor burden is decreased. Additionally, tumors form and develop slower in animals treated with the anti-IL-5 antibody preparation, TRFK-5. The apparent decrease in tumor burden and delay in tumor development, observed in animals treated with TRFK-5 suggest that eosinophils play a role in tumorigenesis and growth. TRFK-5 and/or other inhibitors of eosinophilia might provide a means by which to treat and prevent tumor cell growth. If future studies demonstrate that this result if general, TATE may be used as a prognostic indicator for poor clinical outcome in epithelial tumors.

Previously, it was shown that TRFK-5 could be used in hamsters to block eosinophilic infiltrates in cutaneous wounds (Yang et al., 1997, *Am. J. Pathol.,* 151: 813–819). The data presented in herein show that it also blocks eosinophilia of the stromal tissues, at the leading edge of tumors in the cheek pouch. No animal model has existed up until this point for studying the relationship of eosinophils to developing malignant epithelial lesions. The invention provides such a model, which may be applied to any epithelial tumor by use of the methods described in this Example.

EXAMPLE 2

A rat model of ovarian epithelial cancer is described by Major et al. (1997, *Gynecol. Oncol,* 66: 122–132, the contents of which are herein incorporated by reference). Briefly, pathogen-free Fischer 344 (F344) female rats are injected intraperitoneally with NuTu-19 epithelial cells; these cells are derived from a poorly-differentiated adenocarcinoma which arose in a female athymic mouse after injection of F344 ovarian surface epithelial cells that spontaneously underwent malignant transformation in vitro. Following injection, tumors develop in a manner that mimics human ovarian cancer cell (specifically, papillary serous adenocarcinoma) growth in terms of the method of intraperitoneal spread, the formation of malignant ascites and the propensity for local metastases and the invasion of organs (e.g. the omentum, peritoneum, liver and bowel).

NuTu-19 cells are maintained in complete medium, comprising RPMI 1640 (Gibco Life Technologies; Grand Island, N.Y.) and 10% heat-inactivated fetal bovine serum at 37° C. under 5% $CO_2$. Prior to use, cells are harvested with 0.25% trypsin (Gibco Life Technologies; Grand Island, N.Y.), washed twice with Dulbecco's phosphate-buffered saline (PBS; Gibco Life Technologies), counted for cell number and viability using trypan blue exclusion; each harvested sample exhibits at least 90% cell viability, or it is discarded. Cells are injected intraperitoneally into F344 rats at a concentration of 106 viable cells/ml (1 ml total injected per animal). Control rats receive 1 ml of PBS without cells. After three weeks, tumor cell growth is visualized, both in vivo and ex vivo, as follows:

Animals are anaesthetized by standard procedures and injected intraperitoneally with a sterile solution of 40 mg/ml 5-aminolevulinic acid (ALA), pH 6.5, to a final whole-body concentration of from 50- to 100 mg/kg. At a time between 1.5 and 3 hours post-injection, the rat is placed in a supine position and a laparotomy (xyphoid to pubic symphysis) is made. A fluorescent polymethacrylate disc ($OD_{460}$=0.025; emission maximum near 600 nm) is inserted into the animal as a standard, and fluorescence is induced by application of light from an ultraviolet lamp (e.g. a Model B-100 AP lamp, spectrum 310–395 nm with main emission line at 366 nm; UVP, Inc., San Gabriel, Calif.) positioned approximately 15 cm from the anterior abdominal wall of the animal. Positive fluoresence, indicative of tumor cell growth, is observed as lesions exhibiting an orange/red color that is in contrast with the surrounding tissue. The intensity of fluorescence, which is proportional to tumor burden, is calibrated against the polymethacrylate standard disk.

Following in vivo fluorescent measurement, which serves best to highlight tumor distribution, ex vivo measurement is performed. Animals are euthanized by any approved protocol, e.g. intracardiac injection 0.2 ml of EUTHA-6 (Western Medical Supply; Arcadia, Calif.). Tumor-bearing tissue samples from the abdominal cavity are harvested. An argon-ion laser coupled to a microlens-terminated optical fiber (64 $\mu W/cm^2$ at the sample) is used for fluorescent excitation, and images are recorded using a slow-scan thermoelectrically-cooled CCD camera (e.g. a Model TE/CCD-576 E/UV; Princeton Instruments, Trenton, N.J.). Source distribution and fluorescence images are acquired with 500-nm shortpass and 650-nm (±12.5 nm) bandpass filters (Corion Corporation; Holliston, Mass.), respectively, using 1-second acquisition times. Image acquisition, processing and camera control are performed by a computer equipped with IPLab software (Signal Analytics Corp.; Vienna, Va.). Tissue fluorescence and light distribution images are recorded sequentially for each sample under identical conditions. Dark-noise images are acquired without the excitation source. Images are corrected for both nonuniform illumination and contributing dark noise using the following formula:

$$\text{Corrected fluorescence image} = \frac{\text{Image (650 nm)} - \text{Dark noise (650 nm)}}{\text{Image (500 nm)} - \text{Dark noise (500 nm)}}$$

On the corrected fluorescence image, the mean fluorescence of the peritoneum, the small intestine and tumor nodules on the omentum and peritoneum are measured.

Imaging of frozen tissue sections, taken at the time of euthanasia by standard methods (see again Humason, 1979, supra), is performed using the same cooled CCD camera and computer system; however, the camera is coupled to an epifluorescence microscope (e.g. an Axiovert 10; Carl Zeiss, Inc., Thomwood, N.Y.) equipped with a 100-W mercury lamp filtered with a 405-nm (±20 nm) bandpass filter (Omega Engineering, Inc.; Stamford, Conn.) to provide excitation at this wavelength, and using a dichroic mirror (e.g. an FT 440). A shutter (e.g. a Uniblitz, Model T1 32; Vincent Associates, Rochester, N.Y.) is used to synchronize the CCD camera with the excitation source.

Statistical analysis of fluoresence observed in the experimental animals is performed in order to quantify the tumor growth resulting from the transplanted cells. Differences in fluorescence yield among animals or between groups of animals that are either untreated following cell injection or who receive an inhibitor of eosinophilia according to the invention are analyzed using ANOVA. Statistical significance is taken as $P \leqq 0.05$. If a significant overall difference is present, multiple comparisons are performed using Fisher's PLSD multiple comparison procedure.

In order to assay the effect of inhibiting eosinophilia on ovarian epithelial tumor cell growth using this model, it is necessary to divide test animals into two groups, as discussed above. Animals in each group will receive $10^6$ NuTu-19 cells, as described above. One group will remain untreated, while members of each of the other group receive a candidate inhibitor of eosinophila (e.g. anti-IL-5 antibodies, as discussed in Example 1), delivered intraperitoneally. Administration of the inhibitor may be before, concurrently with or after injection of the tumor cells into the recipient animals, up to the time at which animals are sacrificed for quantitation of tumor cell growth. Depending on the time of administration, the effect of inhibiting eosinophilia either on tumor formation or on reducing an established tumor is seen. The effective concentration of inhibitor to be administered is calculated beginning with the effective topical dosage of the inhibitor applied to a surface site of actual or potential tumor cell growth, as exemplified in Example 1, multiplying the treated area from such an experiment by the estimated surface area of structures within the abdominal cavity and multiplying again by the dilution factor brought about by the volume of fluid estimated to be present around those structures.

The efficacy of a candidate substance to inhibit eosinophilia in the area surrounding ovarian tumors formed by this model is assayed by inducing tumors as described and treating half of the animals receiving cells with the substance at or immediately prior to the time of cell injection with the drug, while the control animals receive carrier solution only. Three weeks later, animals are euthanized; where tumors are observed in the abdominal cavity, the concentration of eosinophils infiltrating adjacent tissues are measured as described in Example 1. A reduction of at least two-fold in eosinophils surrounding sites of tumor formation, if any, in the treated animals relative to controls is indicative of effective blockage of eosinophilia;.

Once it is established that eosinophilia is inhibited by a given substance in sites of ovarian tumor cell formation, its ability to suppress tumor formation, or to reduce tumors that have already formed, is quantitated in several ways using this model:

The extent to which delay in the onset of tumor formation is assayed by injecting female rats with NuTu-19 cells, as described above, treating half of the animals with a dose of the inhibitor sufficient to block eosinophilia and the other half with carrier buffer only (either before- or at the time of cell injection), sacrificing equal numbers of treated and sham-treated animals at each of a number of time-points following treatment and examining their abdominal structures for signs of tumor formation. At each time point, the numbers of test and control animals in whom tumors are observed are noted. At the end of the experiment, the average time of appearance of tumors is calculated for members of each group. By this standard, a delay of at least four-fold is required for an inhibitor of eosinophilia to be judged efficacious in suppressing tumor formation.

If a suppression of tumor burden is instead to be quantitated, the tumors are induced and animals are treated as described above; however, all are sacrificed at once (e.g. three weeks after the introduction of NuTu-19 cells). Tumor tissue in each animal is quantitated fluorescently, and the average amount present in animals of the test group is compared to that observed in controls. A reduction of at least four-fold in average tumor burden is required for treatment to be considered effective.

In either case, comparison of the proportion of animals in each group who remain tumor- free over the course of the experiment resulting in a two-fold or greater increase among treated animals is indicative that the inhibitor is effective at suppressing tumor formation.

Time-points similar to those used to judge the relative rates of tumor formation may be taken using animals treated after tumors have been allowed to form. At T=0, a group of treated and untreated animals is sacrificed, and average tumor burden measured. At time points taken thereafter, animals from both groups are sacrificed and examined as above. A reduction over time of at least 50% in tumor burden or a two-fold reduction in the rate of tumor cell growth in treated animals relative to controls is indicative of effective treatment according to the invention.

EXAMPLE 3

Tumors of the lung epithelium are induced in Beagle dogs via exposure through inhalation of a plutonium-239 aerosol, as previously described (McClellan et al., 1986, In: *Life-Span Radiation Effects Studies in Animals: What Can They Tell Us*?, eds. Thompson and Mahaffey, CONF-830951, pp. 74–96, Office of Scientific and Technical Information, D.O.E., Richland, Wash.). In brief, purebred Beagle doges are exposed to monodisperse aerosols of $^{239}PuO_2$ particles or the aerosol dilutant by brief, single, nose-only exposures. The aeorsol concentration and duration of exposure are adjusted for each animal to achieve a desired projected initial lung burden. After exposure, dogs are observed daily, and complete physical examinations, hematologic studies, clinical chemistry and radiographic surveys are performed annually. A detailed postmortem examination is performed whether at the time of natural death or of euthanasia (performed according to approved protocols for humane reasons). Tissue sections from all organ systems and any observed lesions are fixed in 10% neutral-buffered formalin, stained with eosin and hematoxylin, embedded in paraffin and sectioned at a thickness of 4- to 8 $\mu$m. Portions of any suspected lung tumor along with adjacent normal lung epithelial tissue are frozen in liquid nitrogen and stored at −80° C. prior to fixation of the remainder of the sample. Sectioned samples of normal and abnormal lung tissue are examined by a single investigator in order to ensure uniform identification of cell types, which are judged according to the standard criteria for classification and nomenclature established by the World Health Organization.

Alternatively, visible tumors are excised and their total weight is measured; while this excludes from the analysis tumors too small to be detected and handled in this manner, it provides an approximation of total tumor burden.

In addition to morphological characteristics, the expression of the epidermal growth factor receptor (EGF-R) is a diagnostic feature of lung epithelial cancer cells (which represent a subset of tumor cells observed in this model system), among others. Sections of fixed lung tissue are stained with a commercially-available mouse monoclonal anti-EGF-R immunoglobulin $G_1$ (e.g. 29.1 hybridoma; ICN or Seratec) according to standard methods. Briefly, paraffin-embedded 5-$\mu$m sections are deparaffinized by heating in a 60° C. oven for 1 hour, followed by two 5-minute xylene washes and subsequently rehydrated through decreasing alcohol concentrations (100%, 95% and 50%, 5 minutes each). Endogenous peroxidase activity is blocked by incubating the sections for 1 hour in 0.5% hydrogen peroxide in methanol at room temperature. Sections are then washed in distilled water, followed by Tris-buffered saline (TBS), pH 7.6. Sections are incubated for 20 minutes at room temperature with normal horse serum (1:100 dilution in 0.3% bovine serum albumin in TBS) and blotted. The primary antibody is added at a dilution of 1:1,000 and incubated for 18 hours at 4° C. Bound antibody is detected by the avidinibiotin complex method (Vectastain; Vector Laboratories, Burlingame, Calif.). Formalin-fixed A431 cells are processed in parallel as a positive control, while an irrelevant murine immunoglobulin G polyclonal antibody is identically processed on both the A431 cells and on lung tissue sections. Slides are read by two pathologists in a blind, random fashion and are graded according to distribution and intensity of staining pattern.

A candidate inhibitor of eosinophilia is administered by aerosol inhalation on a semi- weekly basis to half of the dogs who have suffered plutonium exposure, while the other half receive only aerosol dilutant. Varying dosages of the substance are assayed if its effective dosage range is not known for any tissue; however, if a substance such as anti-IL-5, for which an effective dosage is presented in Example 1, is used, the estimated internal surface area of the dogs' lungs is divided by the area treated with that total dosage, which is then is multiplied by the result of that calculation. A correction is made for void volume of the lungs (a certain amount of inhibitor will occupy that space and be exhaled without ever having touched the lung surface) and the substance is administered to the dogs.

During the post-mortem examination, a reduction in the percentage of treated dogs who develop lung epithelial tumors or an overall lessening of tumor burden relative to controls is indicative of efficacy of an inhibitor of eosinophilia at suppressing tumor growth in this model system, as described above.

As presented, this analysis is suited only to measurement of terminal tumor parameters, rather than tracking tumor induction and progression in irradiated dogs; however, a preliminary or continuous in vivo analysis is performed either by standard medical imaging techniques (e.g. heavy metal staining followed by X-ray or other scanning procedures) or, where possible, by bronchoscopic examination of anaesthetized subjects in order to track the growth of lung epithelial tumors that are present in major airways. A significant decrease in the rate of tumor growth observed in treated animals relative to controls is indicative of efficacy of treatment according to the invention. If it is desired to assay the effect of a candidate inhibitor on an established tumor, it may be administered to a subset of the control dogs at any time following in vivo detection of tumors by any imaging method; the observed tumors are then monitored for regression over time. As stated above, a reduction of at least 50% in tumor volume or at least a 2-fold decrease in the rate of tumor growth is indicative of efficacy of the candidate inhibitor of eosinophilia according to the invention.

EXAMPLE 4

The invention is of use in the prevention of epithelial tumors for which a known genetic risk is present. A model system comprising mice that reproducibly develop prostate epithelial tumors has been established (Greenberg et al., 1995, *Proc. Natl. Acad. Sci. U.S.A.,* 92: 3439–3443). These transgenic animals express the gene encoding simian virus 40 (SV40) large tumor T antigen (Tag), which has been found to induce cancer in a number of model systems, regulated by sequences of the rat probasin (rPB)-encoding gene, including 426 bp of 5'-flanking DNA and 28 bp of the 5' untranslated region. Transcription of this transgene occurs in the prostate epithelium.

Mice bearing the rPB/Tag construct develop prostate tumors as early as 10 weeks after birth. An inhibitor of eosinophilia according to the invention, such as an anti-IL-5 antibody, is administered to the prostate gland in an effective dosage, determined as described above, to one group of transgenic animals, while a second group receives only carrier buffer (e.g. physiological saline); due to the small size of the animals to be treated, administration is via local injection, prior to which animals are anaesthetized by any approved protocol. Multiple doses are administered beginning immediately after birth; such doses are given every other- to every fourth day.

At ten weeks after birth, a subset of mice from both the treated and control groups are sacrificed; this procedure is repeated every other week thereafter. The prostate gland is excised and subjected to histological analysis by standard methods (see again Humason, 1979, supra). For example, tissues are fixed in 10% (vol/vol) buffered formalin for 24 hours, dehydrated through an ethanol/xylene series and embedded in a histological support medium, e.g. paraffin. Sections of from 5 to 8 $\mu$m in thickness are taken, affixed to glass slides, deparaffinized, stained with eosin/hematoxylin and examined microscopically. Both structural features (e.g. tumors or other neoplasias) and eosinophil infiltration in the region surrounding prostate epithelial tumors, when present, may be observed simultaneously. If staining is inadequate to detect eosinophils, a subset of the sections is instead stained with Giemsa, as discussed in Example 1. A positive correlation between use of the inhibitor of eosinophils and the absence of eosinophils from prostate tissue (in particular, that surrounding tumor cells) is indicative that the inhibitor is effective in the prostate epithelium; a further correlation between use of the inhibitor and either an average delay in the onset of prostate epithelial tumors among treated individuals relative to untreated controls or a reduction in the overall percentage of treated individuals who develop tumors, again relative to controls, is indicative that the inhibitor of eosinophilia is of use in the invention. Note that while this transgenic mouse model is useful in detecting the presence or absence of tumors, it is not of significant use in detecting reductions in overall tumor burden or changes in the rates of cell division of tumors, in that while mice bearing the transgene almost uniformly develop tumors of the prostate epithelium, the size, placement and type of tumors are found to vary significantly.

EXAMPLE 5

A model of urinary bladder epithelial tumors has been developed in rats. Specifically, highly-inbred RA/Han rats (52nd to 54th inbred generation) have been found to develop urinary bladder epithelial tumors at a high frequency (53.9% of males, 14.4% of females, with incidence peaking at 25 to 30 months of age). As with in the case of the transgenic mouse model of prostate epithelial cancer in Example 4, multiple doses of a candidate inhibitor of eosinophilia according to the invention (such as anti-IL-5 antibodies) or of inhibitor-free carrier buffer are administered to the urinary bladder of male DA/Han rats beginning at birth. Such administration is performed weekly, either by local injection or by urethral catheterization; the dosage of the candidate inhibitor is calculated as described above. 1,000 to 2,000 animals are used. Beginning at age 20 months, groups of both treated and control animals (20 animals per group) are sacrificed. Animals who die spontaneously during the course of the experiment are also subjected to post-mortem analysis. Urinary bladders are histologically preserved in a suitable fixative, as described above, stained (typically with hematoxylin and eosin; alternatively, with Giemsa in order better to visualize eosinophils), mounted in a suitable histological support and sectioned. Sections are microscopically examined for the presence or absence of tumors; positive correlations are sought a) between the use of the candidate inhibitor and a reduction in the local concentration of eosinophils in tissue adjacent to tumors, if present, in treated animals relative to controls and b) use of the inhibitor and a reduction in the percentage of individuals bearing urinary bladder epithelial tumors or the age at which such tumors arise in treated animals relative to controls. As in Example 4, this model is not suitable for assessing the efficacy of a candidate inhibitor of eosinophilia in reducing overall tumor load, the size of individual tumors or the rate of tumor cell division in urinary bladder epithelial tumors, as the types and sizes of tumors observed among mice are highly variable, so as to complicate such a quantitative analysis.

EXAMPLE 6

Squamous metaplasia in the columnar epithelium of the uterine cervix is a condition that typically precedes neoplasia in that tissue. Mice deprived of vitamin-A exhibit hyperproliferation of subcolumnar reserve cells, resulting in a high rate of cervical epithelial metaplasia (Darwiche et al., 1993, *Cancer Res.,* 53: 2287–2299). Ultimately, the formation of metaplastic foci, the preneoplastic lesions of squamous cell carcinoma. Such changes are visible either by standard histological methods or by immunohistochemical or RNA in situ analysis of fixed cervical tissue with antibodies or nucleic acid probes designed to detect diagnostic shifts in the expressed complement of keratins. High-level expression of these markers is indicative of metaplasia.

Female BALB/c and nude mice and their mothers are placed on a vitamin-A deficient test diet (TD 85239; Teklad, Madison, Wis.) at birth of the experimental animals. Animals are weaned at week 3 of age and maintained on the deficient diet for periods of time such that mild (10 weeks for nude mice and 1 weeks for BALB/c mice) and severe (14 weeks for nude mice and 20 weeks for BALB/c mice) vitamin-A deficiency would ensue, as monitored by loss of body weight and liver retinylpalnitate levels. Control mice fed the same diet supplemented with all-trans-retinoic acid (RA) at physiological levels (3 μg RA per g body weight) display a normal epithelial phenotype.

In order to test this assumption and assess the tumor-preventive effects of a candidate inhibitor of eosinophilia, a dose of the inhibitor (e.g. the anti-IL-5 antibody used in Example 1) is topically applied daily to the uterine cervices of test vitamin-A-deficient mice in any of the forms (liquid, ointment, powder, etc.) enumerated above in an amount estimated to be effective based upon the action of the substance in tissues in which its action has been assayed, also as described above. Control vitamin-A-deficient mice are treated with carrier only. After a period of severe vitamin-A deprivation, as defined above, and consequent real or sham treatment with the candidate inhibitor mice are sacrificed and histological examination of sectioned uterine cervical tissue is performed by standard methods (see Humason, 1979, supra). A significant reduction, as defined above, in observed metaplasia is indicative of efficacy of an inhibitor of eosinophilia at suppressing tumor cell growth in the cervix.

Use

The invention is useful in the prevention and treatment of tumor cell growth. It is particularly useful in those instances in which dosage with a known mutagen has occurred, and a site of potential tumor induction may be identified, based either on the site of contact or on empirical data regarding any tissue-specific influence of the substance to which a mammal has been exposed. The invention is also useful in the prevention of tumor cell growth in cases in which an individual has a known genetic propensity for the development of tumors at a particular site. Lastly, the invention is of use in inhibiting the growth of an established tumor, where direct administration of a drug to the site of tumor growth is medically convenient and safe.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method of suppressing tumor cell growth wherein the tumor has eosinophilia infiltration, and wherein said tumor cell growth is promoted by said eosinophilia, said method comprising administering to a mammal in need thereof of an amount of an inhibitor of eosinophilia sufficient to result in suppression of tumor cell growth.

2. The method of claim 1, wherein said mammal is a human.

3. The method of claim 1, wherein said inhibitor inhibits a cytokine that influences the maturation of eosinophils.

4. The method of claim 3, wherein inhibition of said cytokine results in inhibition of eosinophil influx into a site of at which said tumor cell growth may potentially occur.

5. The method of claim 3, wherein inhibition of said cytokine results in inhibition of eosinophil influx into tissue adjacent to tumor cells.

6. The method of claim 1, wherein said inhibitor inhibits a Colony Stimulating Factor (CSF).

7. The method of claim 6, wherein inhibition of said CSF results in inhibition of eosinophil influx into a site at which said tumor cell growth may potentially occur.

8. The method of claim 6, wherein inhibition of said CSF results in inhibition of eosinophil influx into tissue adjacent to tumor cells.

9. The method of claim 6, wherein said CSF is interleukin-5 (IL-5).

10. The method of claim 9, wherein said inhibitor of IL-5 is an anti-IL-5 antibody.

11. The method of claim 1, wherein said tumor comprises cells that are malignant.

12. The method of claim 1, wherein said tumor comprises cells that are epithelial cells.

* * * * *

UNITED STATES PATENT AND TRADEMARK OFFICE

CERTIFICATE OF CORRECTION

PATENT NO. : 6,264,948 B1
DATED : July 24, 2001
INVENTOR(S) : Wong et al.

It is certified that error appears in the above-identified patent and that said Letters Patent is hereby corrected as shown below:

Title page,
Item [73], Assignee, should read:
-- Beth Isreal Deaconess Hospital, Inc. and Predsident and Fellows of Harvard College --.

Signed and Sealed this

Twenty-fifth Day of May, 2004

JON W. DUDAS
*Acting Director of the United States Patent and Trademark Office*